(12) United States Patent
Silverman et al.

(10) Patent No.: US 10,822,301 B2
(45) Date of Patent: Nov. 3, 2020

(54) 3-CARBON SUBSTITUTED 4-AMINOCYCLOPENT-1-ENE-1-CARBOXYLIC ACID COMPOUNDS AS INHIBITORS OF GAMMA-AMINOBUTYRIC ACID (GABA) AMINOTRANSFERASE

(71) Applicant: Northwestern University, Evanston, IL (US)

(72) Inventors: Richard B. Silverman, Winnetka, IL (US); Chi-Li Ni, Evanston, IL (US); Jose Juncosa, Salisbury, MD (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/375,469

(22) Filed: Apr. 4, 2019

(65) Prior Publication Data
US 2019/0315677 A1 Oct. 17, 2019

Related U.S. Application Data

(60) Provisional application No. 62/656,747, filed on Apr. 12, 2018.

(51) Int. Cl.
*C07C 229/48* (2006.01)
*A61P 35/00* (2006.01)
*A61P 25/30* (2006.01)

(52) U.S. Cl.
CPC ............ *C07C 229/48* (2013.01); *A61P 25/30* (2018.01); *A61P 35/00* (2018.01)

(58) Field of Classification Search
CPC .................................................. C07C 229/48
See application file for complete search history.

(56) References Cited

U.S. PATENT DOCUMENTS

| | | | |
|---|---|---|---|
| 5,563,175 A | 10/1996 | Silverman | |
| 6,197,819 B1 | 3/2001 | Silverman | |
| 6,255,345 B1 | 7/2001 | Silverman | |
| 6,794,413 B1 | 9/2004 | Silverman | |
| 8,211,865 B2 | 7/2012 | Ilan | |
| 8,969,413 B2 | 3/2015 | Silverman | |
| 9,603,820 B2 | 3/2017 | Silverman | |
| 9,670,141 B2 * | 6/2017 | Silverman | ............... A61P 3/04 |
| 9,856,231 B2 | 1/2018 | Silverman | |
| 9,993,449 B2 | 6/2018 | Silverman | |
| 2003/0225161 A1 | 12/2003 | Silverman | |
| 2007/0105924 A1 | 5/2007 | Silverman | |
| 2012/0245380 A1 | 9/2012 | Ilan | |
| 2013/0041028 A1 | 2/2013 | Silverman | |
| 2016/0264544 A1 | 9/2016 | Silverman | |
| 2017/0101364 A1 | 4/2017 | Silverman | |
| 2017/0239202 A1 | 8/2017 | Silverman | |
| 2018/0051001 A1 | 2/2018 | Silverman | |
| 2018/0098952 A1 | 4/2018 | Silverman | |
| 2018/0271816 A1 | 9/2018 | Silverman | |

OTHER PUBLICATIONS

Hutchins, R. O.; et al. A Convenient Synthesis of Labile Optically Active Secondary Alkyl Bromides from Chiral Alcohols. J. Org. Chem. 1976, 41, 1071-1073.
Li, K-Y.; et al. Synthesis of Cyclophellitol, Cyclophellitol Aziridine, and Their Tagged Derivatives. Eur. J. Org. Chem. 2014, 6030-6043.
Nielsen, M. K.; et al. PyFluor: A Low-Cost, Stable, and Selective Deoxyfluorination Reagent. J. Am. Chem. Soc. 2015, 137, 9571-9574.
Suganuma, Y.; et al. Stereodefined synthesis of the four possible stereoisomers of 5,18-diHETE. Tetrahedron. 2018, 74, 1151-1159.
Xu, F.; et al. Chlorination/Cyclodehydration of Amino Alcohols with SOCl2: An Old Reaction Revisited. J. Org. Chem. 2008, 73, 312-315.

* cited by examiner

*Primary Examiner* — Golam M Shameem
(74) *Attorney, Agent, or Firm* — Quarles & Brady LLP

(57) ABSTRACT

Disclosed are cyclopentene compounds for use as inhibitors of gamma-aminobutyric acid (GABA) aminotransferase (AT) and/or ornithine aminotransferase (OAT). The disclosed cyclopentene compounds include 3-carbon substituted 4-aminocyclopent-1-ene-carboxylic acid compounds which may be formulated in pharmaceutical composition for treating diseases and disorders associated with GABA-AT and/or OAT activity, including epilepsy, addiction, and hepatocellular carcinoma (HCC).

17 Claims, No Drawings

3-CARBON SUBSTITUTED 4-AMINOCYCLOPENT-1-ENE-1-CARBOXYLIC ACID COMPOUNDS AS INHIBITORS OF GAMMA-AMINOBUTYRIC ACID (GABA) AMINOTRANSFERASE

CROSS-REFERENCE TO RELATED PATENT APPLICATIONS

The present application claims the benefit of priority under 35 U.S.C. 119(e) to U.S. Provisional Application No. 62/656,747, filed on Apr. 12, 2018, the content of which is incorporated herein by reference in its entirety.

STATEMENT REGARDING FEDERALLY SPONSORED RESEARCH OR DEVELOPMENT

This invention was made with government support under DA030604 awarded by the National Institutes of Health. The government has certain rights in the invention.

BACKGROUND

The field of the invention relates to cyclopentene compounds for use as inhibitors of gamma-aminobutyric acid (GABA) aminotransferase (AT) and/or ornithine aminotransferase (OAT). In particular, the field of the invention relates to 3-carbon substituted 4-aminocyclopent-1-ene-carboxylic acid compounds for use as inhibitors of GABA-AT and/or OAT, which are formulated as pharmaceutical compositions for treatment of epilepsy, addiction, or hepatocellular carcinoma (HCC).

Gamma-Aminobutyric acid (GABA) is the major inhibitory neurotransmitter in the central nervous system. GABA is produced in presynaptic GABAergic neurons from L-glutamate by the enzyme glutamic acid decarboxylase (GAD). GABA is then released by the presynaptic GABAergic neurons into the synapse and transported to glial cells. In glial cells, the enzyme GABA aminotransferase (GABA-AT), a pyridoxal 5'-phosphate (PLP)-dependent enzyme, degrades GABA to succinic semialdehyde (SSA), which is further oxidized to succinate and enters the Krebs cycle. GABA-AT also converts α-ketoglutarate from the Krebs cycle to L-glutamate. Because there is no GAD in glial cells, this newly formed L-glutamate is not converted to GABA. It is instead converted to L-glutamine by glutamine synthetase, which is then released from glial cells into the synapse and transported back to GABAergic neurons to complete the metabolic cycle of L-glutamate.

After GABA is released from presynaptic GABAergic neurons, GABA binds to chloride-selective ion channel receptors including ($GABA_A$ and $GABA_C$) and to G-protein coupled receptors that are linked to potassium-selective ion channels including ($GABA_B$). Binding of GABA to these receptors causes the receptors to selectively conduct their respective ions and hyperpolarize the postsynaptic membrane, thereby controlling neuronal activity downwardly. Low levels of GABA are linked to many neurological disorders, including epilepsy, Parkinson's disease, Alzheimer's disease, Huntington's disease, and cocaine addiction.

GABAergic drugs are those that improve secretion or transmission of GABA. These drugs as a family have been used to treat a wide variety of nervous system disorders including fibromyalgia, neuropathy, migraines related to epilepsy, restless leg syndrome, and post traumaticpost-traumatic stress disorder. GABAergic drugs include $GABA_A$ and $GABA_B$ receptor ligands, GABA reuptake inhibitors, GABA aminotransferase inhibitors, GABA analogs, or molecules containing GABA itself.

In 1998, a novel strategy was developed for the treatment of cocaine addiction by inhibiting the activity of gamma-aminobutyric acid aminotransferase (GABA-AT). GABA-AT inhibition raises GABA levels, which antagonizes the rapid release of dopamine in the nucleus accumbens (NAcc), a neurochemical response to cocaine and other drugs of abuse. Following this strategy, vigabatrin was developed as an inactivor of GABA-AT and currently is the only FDA-approved inactivator of GABA-AT.

Vigabatrin is currently used as an antiepilepsy drug, and vigabatrin has been successful in the treatment of addiction in animal models for cocaine, nicotine, methamphetamine, heroin, and alcohol. Vigabatrin also was effective in the treatment of cocaine addiction in humans, with up to 28% of patients achieving abstinence in a 9-week double-blind trial. The potential of vigabatrin for general therapeutic use, however, may be problematic. In order to treat epilepsy, a large dose of vigabatrin (~1-3 g) needs to be taken daily, and there are many serious side effects that arise from its usage. Permanent vision loss has been reported to arise from its long-term administration in 25-40% of epilepsy patients resulting from the damage of the retinal nerve fiber layer. Negative psychological effects also have been observed in patients treated with vigabatrin. As a result, the search for an alternative to vigabatrin in the treatment of epilepsy has been an ongoing concern in the art.

One strategy for new inhibitors of GABA-AT relates to the design of mechanism-based inactivators, in particular, the design of unreactive compounds that require GABA-AT catalysis to convert the unreactive compounds into a species that inactivates the enzyme. Because these molecules are not initially reactive, but require the catalytic activity of GABA-AT to become activated and form covalent bonds, indiscriminate reactions with off-target proteins, leading to undesired side effects, should be greatly reduced. Even at lower dosages, these inactivators should be able to achieve the desired pharmacologic effects with enhanced potency and selectivity than conventional inhibitors.

Another pyridoxal 5'-phosphate (PLP)-dependent enzyme belonging to the same evolutionary subgroup as GABA-AT is the enzyme ornithine aminotransferase (OAT). These two enzymes share a high structural homology and, like all aminotransferases, also have very similar catalytic mechanisms. OAT is expressed in many tissues, including liver, kidney, small intestine, brain, and eye and catalyzes the reversible conversion of ornithine and α-ketoglutarate to L-glutamate semialdehyde which cyclizes to $δ_1$-pyrroline-5-carboxylate and L-glutamate. L-glutamate is then converted by glutamine synthetase to L-glutamine. Glutamine is the most abundant free amino acid in the body; it is essential for growth of both normal and neoplastic cells. However, tumor cells take up glutamine more efficiently than normal cells, and tumor growth is enhanced by glutamine. With respect to glutamine, cancer cells distinguish themselves from normal cells in that they have an increased requirement for glutamine to support anabolic processes that stimulate proliferation. Because of the structural similarities between OAT and GABA-AT, it has been shown that some inactivators of GABA-AT also inactivate OAT. Therefore, the compounds disclosed herein as inactivators of GABA-AT may also be used to modulate, reduce and/or inhibit OAT activity and may be useful in the treatment of malignant pathologic proliferative disorders, including but not limited to hepatocellular carcinoma (HCC).

SUMMARY

Disclosed are cyclopentene compounds, pharmaceutical compositions and methods of treating diseases or disorders associated with aminotransferase activity including gamma-aminobutyric acid aminotransferase (GABA-AT) activity and/or ornithine aminotransferase (OAT) activity. Diseases and disorders treated by the disclosed compounds, pharmaceutical compositions, and methods include neurological and psychological diseases and disorders such as epilepsy and addiction as well as cell proliferation diseases and disorders such as hepatocellular carcinoma (HCC).

The disclosed cyclopentene compounds include 3-carbon substituted 4-aminocyclopent-1-ene-1-carboxylic acid compounds. The disclosed compounds may have a formula as follows:

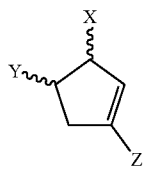

where: X is halo (e.g., F, Cl, Br, or I) or hydroxyl; Y is amino, ammonio, or protected amino; and Z is carboxyl, carboxylate, or protected carboxyl, in which X and Y can have either R- or S-stereochemistry. Also contemplated are salts of the disclosed compounds including pharmaceutically acceptable salts of the disclosed compounds.

Specifically, the disclosed compounds may have a formula:

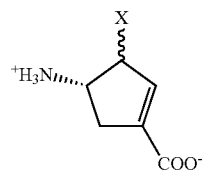

wherein X is halo (e.g., any of F, Cl, Br, and I) or hydroxyl, either R- or S-stereochemistry. The compound may be in the form of an ammonium salt having a counter ion that is the conjugate base of a protic acid.

The disclosed compounds may be formulated as pharmaceutical compositions comprising the compounds or pharmaceutically acceptable salts thereof in a pharmaceutically acceptable carrier for treatment methods for a subject in need thereof. The disclosed compounds and pharmaceutical compositions may be utilized to treat diseases, disorders, or addictions associated with gamma-aminobutyric acid aminotransferase (GABA-AT) activity. The disclosed compounds and pharmaceutical compositions may be utilized to treat modulate dopamine levels in a subject in need thereof. The disclosed compounds and pharmaceutical compositions may be utilized to treat substance addiction in a subject in need thereof. The disclosed compounds and pharmaceutical compositions may be utilized to treat neurological or psychological disease or disorder in a subject in need thereof.

The disclosed compounds and pharmaceutical compositions also may be utilized to treat a subject having a disease or disorder associated with ornithine aminotransferase (OAT) activity. The disclosed compounds and pharmaceutical compositions also may be utilized to treat cell proliferative diseases and disorders such as cancers.

DETAILED DESCRIPTION

The present invention is described herein using several definitions, as set forth below and throughout the application.

Definitions

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a substituent" should be interpreted to mean "one or more substituents," unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

A "subject in need thereof" as utilized herein refers to a subject in need of treatment for a disease, disorder, or addiction associated with gamma-amino butyric acid aminotransferase (GABA-AT) activity and/or ornithine aminotransferase (OAT) activity. The term "subject" may be used interchangeably with the terms "individual" and "patient" and includes human and non-human mammalian subjects.

Diseases and disorders associated with GABA-AT activity may include, but are not limited to, neurological and psychological diseases and disorders. Neurological disorders may include, but are not limited to epilepsy, partial seizures, complex partial seizures, secondary generalized seizures, tonic-clonic seizures, succinic semialdehyde dehydrogenase deficiency (SSADHD), infantile spasms in West's syndrome, Lennox-Gastaut syndrome, tubulous sclerosis, Tourette's syndrome, movement disorders, fibromyalgia, neuropathic pain, migraine related to epilepsy, restless leg syndrome and post-traumatic stress disorder, addiction, obesity, obsessive-compulsive disorders and Alzheimer's disease, and combinations thereof. Psychological disorders may include, but are not limited to, general anxiety disorder, pathological or compulsive gambling disorder, compulsive eating, body dysmorphic disorder, hypochondriasis, pathologic grooming conditions, kleptomania, pyromania, attention deficit hyperactivity disorder and impulse control disorders and combinations thereof.

Diseases and disorders associated with GABA-AT activity may include substance addiction. Substance addictions treated by the disclosed methods may include addictions to one or more of cocaine, heroin, alcohol, barbiturates, amphetamines, cannabis, methadone, opioids, stimulants, nicotine, and combinations thereof.

Diseases and disorder associated with OAT activity may include, but are not limited to, cell proliferative diseases and disorders such as cancers. Cancers may include, but are not limited to, liver cancers such as hepatocellular carcinoma (HCC).

The disclosed compounds may be utilized to modulate enzyme activities including, but not limited to GABA-AT activity and OAT activity. The term "modulate" should be interpreted broadly to include "inhibiting" enzyme activity and/or otherwise modulating enzyme activity.

Chemical Entities

The term "alkyl" as used herein refers to a saturated straight or branched hydrocarbon, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group. An exemplary alkylene group is —CH$_2$CH$_2$—.

The term "haloalkyl" refers to an alkyl group that is substituted with at least one halogen, for example, —CH$_2$F, —CHF$_2$, —CF$_3$, —CH$_2$CF$_3$, —CF$_2$CF$_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxyl" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively. A "cycloalkene" is a compound having a ring structure (e.g., of 3 or more carbon atoms) and comprising at least one double bond.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of an cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form —R$^1$C(O)N(R$^2$)—, —R$^1$C(O)N(R$^2$)R$^3$, —C(O)N(R$^2$)R3, or —C(O)NH$_2$, wherein R$^1$, R$^2$ and R$^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereo isomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

Pharmaceutical Compositions and Formulations

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that modulates GABA-AT activity may be administered as a single compound or in combination with another compound that modulates GABA-AT or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated GABA-AT activity and/or OAT activity. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with GABA-AT activity and/or OAT activity.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

Cyclopentene Compounds and Uses Thereof

Disclosed herein are cyclopentene compounds, pharmaceutical compositions comprising the compounds, and methods of using the compounds and pharmaceutical compositions for treating diseases and disorders associated with GABA-AT activity and/or OAT activity. The disclosed cyclopentene compounds may include 3-carbon substituted 4-amino-cyclopent-1-ene-1-carboxylic acid compounds or salts thereof having a formula as follows:

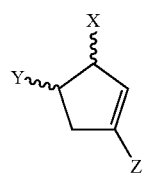

where:

X is halo (e.g., F, Cl, Br, or I) or hydroxyl; Y is amino, ammonio, or protected amino; and Z is carboxyl, carboxylate, or protected carboxyl, in which X and Y can have either R- or S-stereochemistry. Hydrates of the disclosed compounds also are contemplated herein.

The disclosed compounds in particular may have a formula:

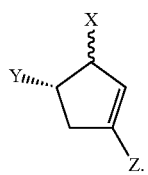

In some embodiments, the disclosed compounds may have a formula selected from:

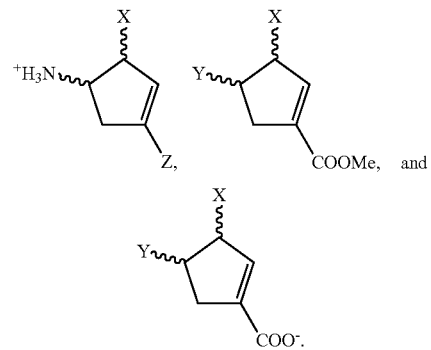

In other embodiments, the disclosed compound may have a formula selected from:

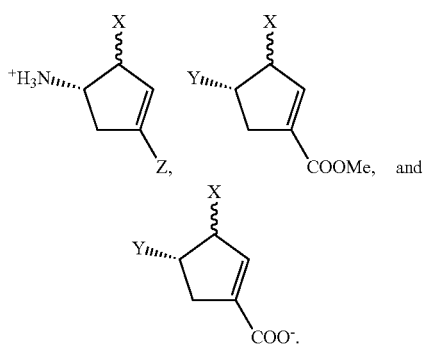

Specifically, the disclosed compounds may have a formula:

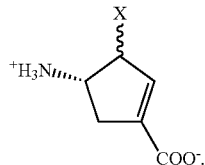

The disclosed compounds may include one or more protecting groups, including protecting groups for an amino group of the compounds and/or protecting groups for the carboxyl group of the compounds. In some embodiments, the disclosed compound have a formula:

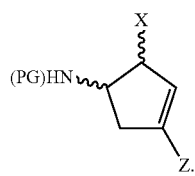

where PG is a protecting group optionally selected from tert-butoxylcarbonyl (Boc), 9-fluorenylmethoxcarbonyl (Fmoc), benzyloxycarbonyl or carboxybenzyl or carbobenzyloxy (Cbz), acetyl (Ac), trifluoroacetyl, phthalic anhydride, benzyl (Bn), benzoyl (Bz), triphenylmethyl (Tr), benzylidenyl, p-toluenesulfonyl (Ts), p-methoxybenzyl carbonyl (Moz or MeOZ), p-methoxybenzyl (PMB), 3,4-dimethoxybenzyl (DMPM), p-methoxyphenyl (PMP), and trichloroethyl chloroformyl (Troc).

In other embodiments, the disclosed compounds have a formula:

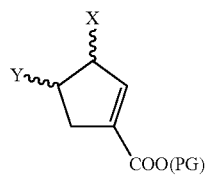

where PG is a protecting group optionally selected from alkyl such as methyl or tert-butyl, aryl such as benzyl, 2-6-disubstituted phenyls such as 2,6-dimethylphenol, 2,6-diisopropylphenol, and 2,6-di-tert-butylphenol, and silyl.

In some embodiments, amino-protected and/or carboxy-protected compounds may include compounds having a formula selected from:

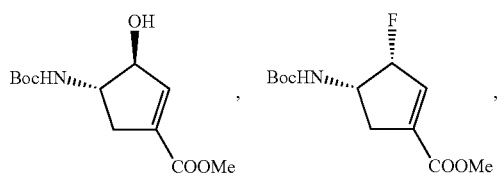

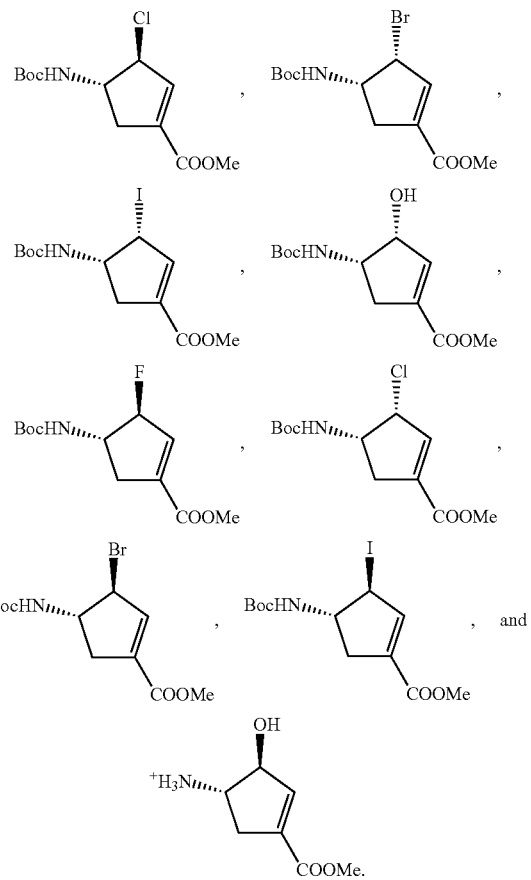

Specifically, the compounds disclosed herein may include compounds having a formula selected from:

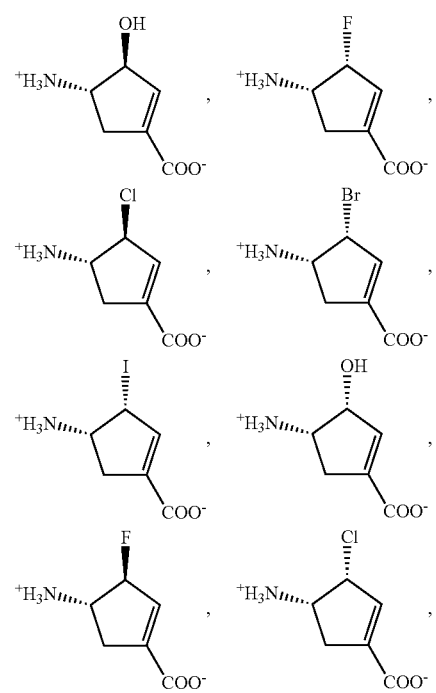

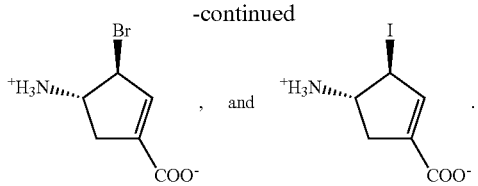

Salts of the disclosed compounds are contemplated herein. In some embodiments, where the compounds include a 4-ammonio group, the compound is an ammonium salt having a counter ion that is the conjugate base of a protic acid.

The disclosed compounds, salts thereof, and/or hydrates thereof may be formulated as pharmaceutical compositions comprising the compounds, salts thereof, and/or hydrates thereof, in a pharmaceutically acceptable carrier. The pharmaceutical compositions may be formulated for treating diseases or disorders associated with GABA-AT activity and/or OAT activity.

In some embodiments, the disclosed compounds and pharmaceutical compositions may be utilized for treating a subject having a disease, disorder, or addiction associated with gamma-aminobutyric acid aminotransferase (GABA-AT) activity, the method comprising administering to the subject the compounds and/or the pharmaceutical compositions. In these methods, the subject may be administered an amount of the compound sufficient to modulate GABA-AT activity.

In some embodiments, the disclosed compounds and pharmaceutical compositions may be utilized for modulating dopamine levels in a subject in need thereof. In these methods, the subject may be administered an amount of the compound sufficient to modulate GABA-AT activity. In these methods, the modulated dopamine levels may be responsive to ingestion of an addictive substance and preferably the method treats excessive dopamine release in the subject in response to ingestion of the addictive substance In some embodiments, the disclosed compounds and pharmaceutical compositions may be utilized for treating substance addiction in a subject in need thereof. In these methods, the subject may be administered an amount of the compound sufficient to modulate GABA-AT activity. In these methods, the subject may be addicted to a substance selected from, but not limited to, the group consisting of cocaine, heroin, alcohol, barbiturates, amphetamines, cannabis, methadone, opioids, stimulants, nicotine, and combinations thereof.

In some embodiments, the disclosed compounds and pharmaceutical compositions may be utilized for treating a neurological or psychological disease or disorder in a subject in need thereof. In these methods, the subject may be administered an amount of the compound sufficient to modulate GABA-AT activity. In these methods, the disease or disorder may be a neurological disorder optionally selected from the group consisting of, but not limited to, epilepsy, partial seizures, complex partial seizures, secondary generalized seizures, tonic-clonic seizures, succinic semialdehyde dehydrogenase deficiency (SSADHD), infantile spasms in West's syndrome, Lennox-Gastaut syndrome, tubulous sclerosis, Tourette's syndrome, movement disorders, fibromyalgia, neuropathic pain, migraine related to epilepsy, restless leg syndrome and post-traumatic stress disorder, addiction, obesity, obsessive-compulsive disorders and Alzheimer's disease, and combinations thereof. In these methods, the disease or disorder may be a psychological disorder optionally selected from, but not limited to, the group consisting of general anxiety disorder, pathological or compulsive gambling disorder, compulsive eating, body dysmorphic disorder, hypochondriasis, pathologic grooming conditions, kleptomania, pyromania, attention deficit hyperactivity disorder and impulse control disorders and combinations thereof.

In some embodiments, the disclosed compounds and pharmaceutical compositions are utilized in methods for treating a subject having a disease or disorder associated with ornithine aminotransferase (OAT) activity, the method comprising administering to the subject the compounds or the pharmaceutical compositions. In these methods, the subject may be administered an amount of the compound sufficient to modulate OAT activity. In these methods, the methods may reduce OAT activity and glutamate production characterized by OAT activity. These methods may be utilized for treating cell proliferative diseases and disorders including, but not limited to, cancers. In particular, the disclosed compounds and pharmaceutical compositions may be administered in methods for treating liver cancers, such as hepatocellular carcinoma (HCC).

EXAMPLES

The following Examples are illustrative and are not intended to limit the scope of the claimed subject matter.

Title—Cyclopentene Inhibitors of GABA Aminotransferase

Epilepsy, a disease defined by recurrent episodes of seizures, affects up to 2% of the world population. Drugs used in the treatment of epilepsy need to cross the blood-brain barrier, which is a membrane that protects the central nervous system. Treatments for epilepsy depend on the inactivation of GABA-aminotransferase. Currently, the most commonly used FDA-approved drug for infantile spasms is vigabatrin. However, this drug produces many undesirable side effects, including an irreversible loss of vision. This class of cyclopentene compounds seeks to irreversibly inhibit GABA aminotransferase via a mechanism that potentially minimizes the formation of highly reactive metabolites that have been hypothesized to cause harmful side effects. As such, this class of cyclopentene compounds may be formulated in pharmaceutical compositions for treating diseases and disorders associated with GABA aminotransferase activity such as epilepsy with less severe side effects as compared to existing medications such as vigabatrin.

Cyclopentene Synthesis (1S,4R)—N-tert-Butyloxycarbonyl-2-azabicyclo[2.2.1]hept-5-en-3-one (2). To a solution of 2-azabicyclo[2.2.1]-hept-5-en-3-one (2.00 g, 18.3 mmol) dissolved in 20 mL $CH_2Cl_2$ was added $Boc_2O$ (4.67 g, 21.4 mmol), DMAP (0.024 g, 0.20 mmol), and triethylamine (3 mL, 21.5 mmol). The reaction mixture was stirred for 3 h at 0° C. Then the mixture was poured into water (20 mL) and extracted with $CH_2Cl_2$ (3×20 mL). The organic layers were combined, dried with sodium sulfate, decanted, and concentrated. The residue was purified by column chromatography (0-33% ethyl acetate/hexanes) to obtain the product (2) as a white solid (3.15 g, 82%).

(1R,2S,4R,5S)-7-Oxo-3-oxa-6-azatricyclo[3.2.1.0$^{2,4}$]octane-6-carboxylic acid tert-butyl ester (3). To a solution of (2) (2.92 g, 14.0 mmol) dissolved in 100 mL $CH_2Cl_2$ was added mCPBA (9.41 g, 42.0 mmol). The reaction mixture was stirred at room temperature for 24 h, after which cyclopentene (2.7 mL, 2.2 eq) was added to the flask, along with 80 mL $CH_2Cl_2$, and the mixture was allowed to stir overnight. The mixture was concentrated and dissolved in 75 mL CH$_2$Cl$_2$, and then washed with a saturated NaHCO$_3$ solution (3×75 mL). The organic layer was dried with sodium sulfate, decanted, and concentrated. The residue was purified by column chromatography (30% hexanes/ethyl acetate) to obtain the product (3) as a white solid (2.11 g, 67%).

(3S,4S)-4-((tert-Butoxycarbonyl)amino)-3-hydroxycyclopent-1-ene-1-carboxylic acid methyl ester (4). To a solution of (3) (1.90 g, 8.44 mmol) dissolved in 20 mL of methanol at 0° C. was added sodium methoxide (0.5 M in MeOH, 1.7 mL). The reaction mixture was allowed to reach room temperature and stirred for 24 h. Then 2 mL of a saturated NH$_4$Cl solution was added to the mixture, and was stirred for 15 minutes. The mixture was concentrated and to it was added 40 mL CH$_2$Cl$_2$. It was then washed with 20 mL of a saturated NaHCO$_3$ solution. The organic layer was dried with sodium sulfate, decanted, and concentrated. The residue was purified by column chromatography (10-30% ethyl acetate/hexanes) to obtain the product (4) as a white solid (1.35 g, 62%).

(1S,2S)-2-Hydroxy-4-(methoxycarbonyl)cyclopent-3-en-1-aminium trifluoroacetate (5). To the Boc-protected amine (0.500 g, 1.94 mmol) was added 5 mL TFA and 5 mL CH$_2$Cl$_2$. The reaction was allowed to stir for one day, and the TFA/CH$_2$Cl$_2$ was evaporated. The crude product was used in the next step without further purification.

(3S,4S)-4-Ammonio-3-hydroxycyclopent-1-ene-1-carboxylate (6). To a solution of (5) in water was added sodium hydroxide to reach pH 12. The reaction was allowed to stir for 2 days. Then, the reaction mixture was brought to pH 2, and concentrated. The residue was purified by reverse-phase column chromatography to yield (6) (yield not determined).

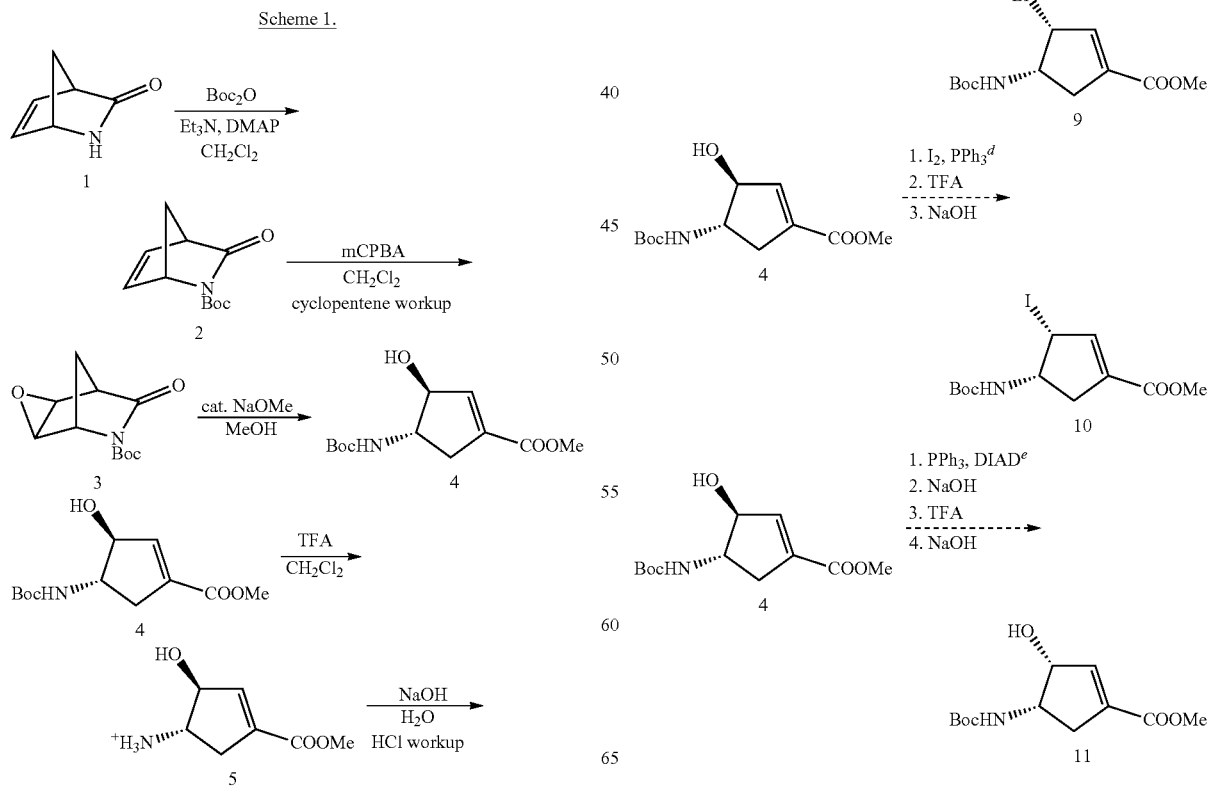

Scheme 2.

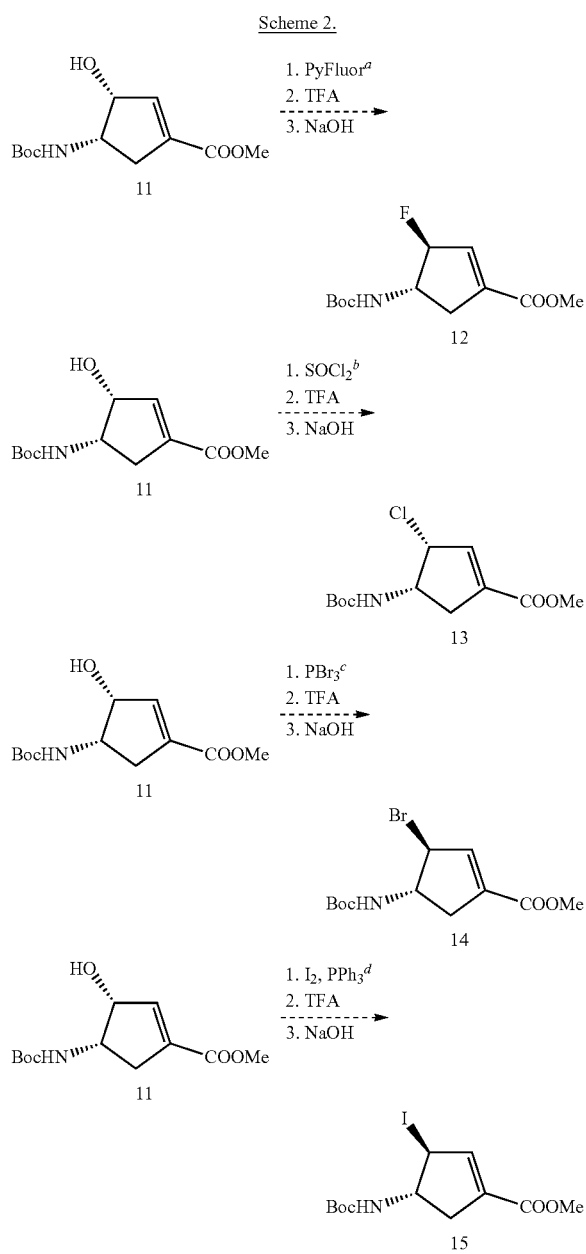

a: Nielsen, M. K.; Ugaz, C. R.; Li, W.; Doyle, A. G. PyFluor: A Low-Cost, Stable, and Selective Deoxyfluorination Reagent. J. Am. Chem. Soc. 2015, 137, 9571-9574.
b: Xu, F.; Simmons, B.; Reamer, R. A.; Corley, E.; Murry, J.; Tschaen, D. Chlorination/Cyclodehydration of Amino Alcohols with SOCl$_2$: An old Reaction Revisited. J. Org. Chem. 2008, 73, 312-315.
c: Hutchins, R.O.; Masilamani, D.; Maryanoff, C. A. A. Convenient Synthesis of Labile Optically Active Secondary Alkyl Bromides from Chiral Alcohols. J. Org. Chem. 1976, 41, 1071-1073.
d: Li, K-Y.; Jiang, J.; Witte, M.D.; Kallemeijn, W. W.; van den Elst, H.; Wong, C-S.; Chander, S. D.; Hoogendoorn, S.; Beenakker, T. J. M.; Codee, J. D. C.; Aerts, J. M. F. G.; van der Marel, G. A.; Overkleeft, H. S. Synthesis of Cyclophellitol, Cyclophellitol Aziridine, and Their Tagged Derivatives. Eur. J. Org. Chem. 2014, 6030-6043.
e: Suganuma, Y.; Tanabe, S.; Sugihara, Y.; Kobayashi, Y. Stereodefined synthesis of the four possible stereoisomers of 5,18-diHETE. Tetrahedron. 2018, 74, 1151-1559.
Note: Procedures for TFA and NaOH deprotections come from procedures given for the synthesis of 6.

In the foregoing description, it will be readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound having a formula as follows or salts thereof:

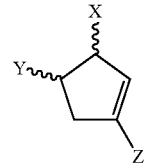

wherein:

X is halo or hydroxyl;

Y is amino, ammonio, or protected amino;

wherein X and Y can have either R- or S-stereochemistry; and

Z is carboxyl, carboxylate, or protected carboxyl.

2. The compound of claim 1 having a formula:

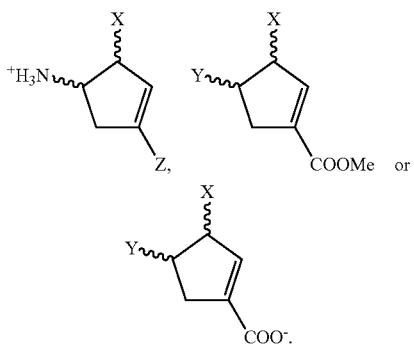

3. The compound of claim 1 having a formula:
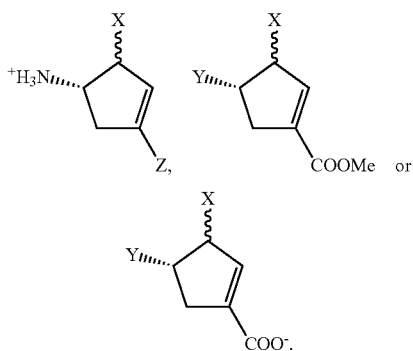
4. The compound of claim 1 having a formula:
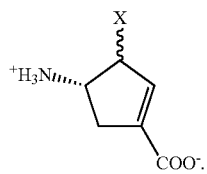
5. The compound of claim 1 having a formula:
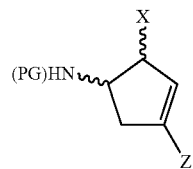
wherein PG is a protecting group.
6. The compound of claim 1 having a formula:
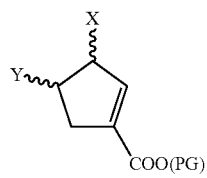
wherein PG is a protecting group.
7. The compound of claim 1 having a formula selected from:
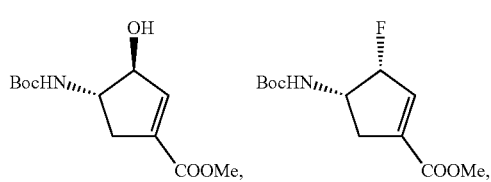
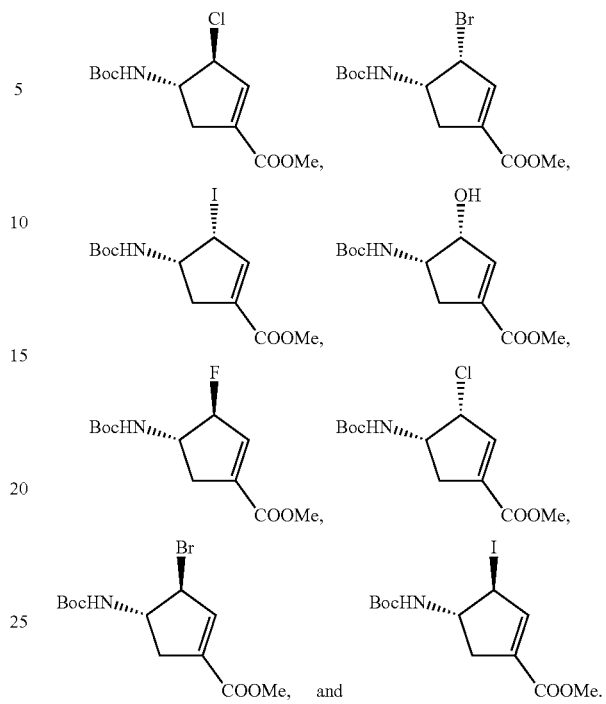
8. The compound of claim 1 having a formula selected from:
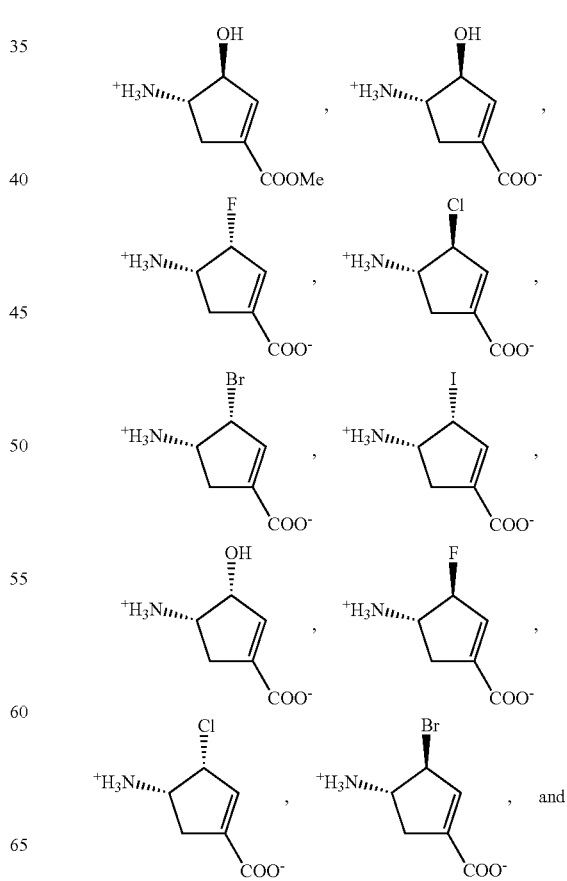

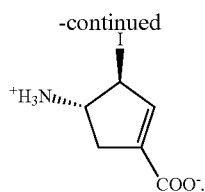

9. The compound of claim 1, wherein X is ammonio and the compound is an ammonium salt having a counter ion that is the conjugate base of a protic acid.

10. A pharmaceutical composition comprising the compound of claim 1 or a pharmaceutically acceptable salt thereof in a pharmaceutically acceptable carrier.

11. The compound of claim 1 having a formula:

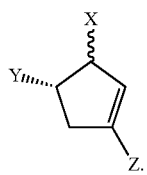

12. The compound of claim 11 having a formula:

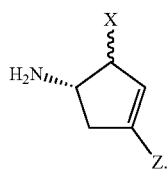

13. The compound of claim 11 having a formula:

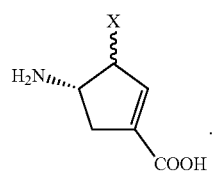

14. The compound of claim 11 having a formula selected from:

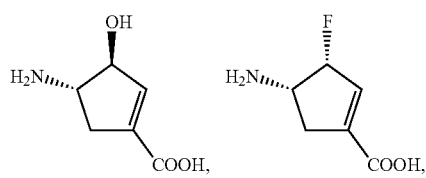

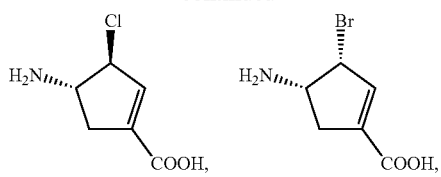

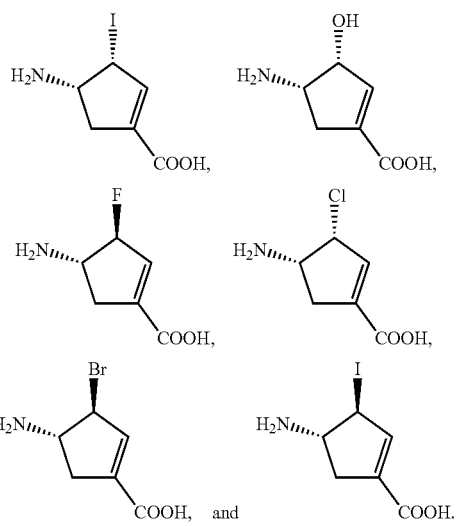

15. A pharmaceutical composition comprising the compound of claim 11 or a pharmaceutically acceptable salt thereof in a pharmaceutically acceptable carrier.

16. A compound having a formula as follows or salts thereof:

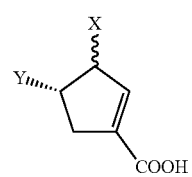

wherein:

X is halo or hydroxyl;

Y is amino, ammonio, or protected amino; and wherein X can have either R- or S-stereochemistry.

17. A pharmaceutical composition comprising the compound of claim 16 or a pharmaceutically acceptable salt thereof in a pharmaceutically acceptable carrier.

* * * * *